United States Patent [19]

King, Jr. et al.

[11] Patent Number: 5,142,086
[45] Date of Patent: Aug. 25, 1992

[54] METHOD FOR MAKING ORGANIC CARBONATES

[75] Inventors: Joseph A. King, Jr., Schenectady, N.Y.; Terry E. Krafft, Longmont, Colo.; Gary R. Faler, Scotia, N.Y.

[73] Assignee: General Electric Company, Schenectady, N.Y.

[21] Appl. No.: 678,411

[22] Filed: Apr. 1, 1991

[51] Int. Cl.$^5$ .................. C07C 68/00; C07C 69/96
[52] U.S. Cl. ......................... 558/274; 558/265; 558/268; 558/271; 558/276; 558/277
[58] Field of Search ............ 558/274, 277, 268, 271, 558/265, 276

[56] References Cited

U.S. PATENT DOCUMENTS 3,994,960 11/1976 Yamazaki et al. ............ 558/277
4,096,168 6/1978 Hallgren ...................... 558/274
4,187,242 2/1980 Chalk ........................... 558/271
4,349,485 9/1982 Hallgren ...................... 558/274

*Primary Examiner*—Vivian Garner
*Attorney, Agent, or Firm*—William A. Teoli; James C. Davis, Jr.; William H. Pittman

[57] ABSTRACT

A method for making diphenyl carbonate free of color bodies is provided by reacting an organic hydroxy compound, such as phenol with carbon monoxide and oxygen in the presence of an effective amount of a palladium catalyst, in the form of a palladium material which is used in combination with a quaternary ammonium salt, an inorganic cocatalyst, such as cobalt diacetate and an organic cocatalyst such as benzophenone or 1,10-phenanthroline. Recycling of catalyst values is also provided.

7 Claims, No Drawings

METHOD FOR MAKING ORGANIC CARBONATES

REFERENCE TO COPENDING APPLICATIONS

Reference is made to copending applications of T. C. T. Chang, Ser. No. 07/607,773, filed Oct. 31, 1990, which is a continuation of Ser. No. 217,257, filed Jul. 11,1988, now abandoned; Ser. No. 07/609,133, filed Nov. 5, 1990, now abandoned which is a continuation of Ser. No. 217,248, filed Jul. 11, 1988, now abandoned; and copending application Ser. No. 07/503,404, filed Apr. 2, 1990.

BACKGROUND OF THE INVENTION

The present invention relates to a method for making organic carbonates by reacting an organic hydroxy compound, such as phenol, with carbon monoxide and oxygen in the presence of a palladium catalyst, a quaternary ammonium salt, and a cocatalyst of a metallic material, such as a cobalt salt, and an organic material such as benzophenone. More particularly, the present invention relates to a method for making diphenyl carbonate which provides a means for recycling catalyst values and minimizes the production of color bodies resulting from the decomposition of particular organic cocatalyst components.

J. E. Backvall, et al, show in their publication, Biomimetic Aerobic 1,4-Oxidation of 1,3-Dienes Catalyzed by Cobalt Tetraphenylporphyrin-Hydroquinone-Palladium (II), An Example of Triple Catalysis, J. Am. Chem. Soc. 1987, 109, 4750–4752, the use of macrocyclic metal complexes employing p-benzoquinone-hydroquinone as a catalytic electron carrier in oxidation reactions and palladium catalyzed oxidations of conjugated dienes. There also is shown by T. C. T. Chang, copending application Ser. No. 07/607,773, a method for making organic carbonates utilizing an organic hydroxy compound with carbon monoxide and oxygen and a catalyst in the form of elemental or chemically combined palladium, cobalt, tetraalkylammonium halide and at least one quinone, an aromatic diol reduction product or mixture thereof. In T. C. T. Chang copending application Ser. No. 217,248, filed Jul. 11, 1988, there is shown a method of making organic carbonates utilizing a similar procedure as Ser. No. 07/607,773 except that in place of chemically combined cobalt, there is utilized divalent or trivalent manganese.

In copending application 07/503,404, filed Apr. 2, 1990, there is shown a method for making organic carbonates employing an organic hydroxy compound, such as phenol, carbon monoxide and oxygen in the presence of an effective amount of a palladium catalyst and carbon dioxide as a desiccant. As taught in Ser. No. 07/503,404, there can be used in combination with the palladium catalyst, such as palladium(II) acetate, a tetraalkylammonium halide and at least one quinone and aromatic diol formed by the reduction of said quinone or a mixture thereof. In addition, a manganese or cobalt cocatalyst also can be used.

Although the aforementioned methods for making organic carbonates are of interest because they do not require the use of phosgene which is a toxic and irritating gas, experience has shown that recycling of catalyst values and/or recovery of the organic carbonate free of color bodies is often not feasible. It is believed that the use of quinones such as hydroquinones causes catalyst deactivation. Attempts to recycle catalyst values free of impurities after separation of organic carbonate is rendered difficult because of the quinone breakdown during carbonylation. It would be desirable therefore to provide a method for making organic carbonates without the use of phosgene, while permitting a recycling of catalyst values, along with a simplified recovery of product free of color bodies.

SUMMARY OF THE INVENTION

The present invention is based on the discovery that if in the palladium catalyzed oxidation of organic hydroxy compounds to organic carbonates, quinones, such as benzoquinone or hydroquinone which mediate oxidative-reductive electron transport, are replaced by ketones, such as benzophenone, or methyl phenyl ketone, or aromatic polycyclic coal tar hydrocarbons, such as anthracene, that the carbonylation of organic hydroxy compound can be satisfactorily achieved along with the recycling of catalyst values, and the recovery of the organic carbonate substantially free of color bodies.

STATEMENT OF THE INVENTION

There is provided by the present invention, a method for making an organic carbonate which comprises, (1) contacting an organic hydroxy compound with a mixture of carbon monoxide and oxygen at a temperature of from about 50° C. to about 170° C. and at a pressure from about 100 psi to about 5000 psi in the presence of an amount of a palladium catalyst which is effective as a carbonylation catalyst comprising, (a) palladium material, (b) a quaternary ammonium salt, (c) a metallic cocatalyst material selected from a class of metals or compounds of metals consisting of cobalt, iron, cerium, manganese, molylidenum, samarium, vanadium, chromium and copper, and, (d) an organic cocatalyst selected from a class of materials consisting of aromatic ketones, aliphatic ketones and aromatic polycyclic coal tar hydrocarbons, (2) distilling the mixture of (1) at a temperature of at least about 45° C. and at a pressure of at least about 1 torr to effect the removal of the organic hydroxy compound, (3) distilling the mixture of (2) at a temperature of at least about 120° C. and at a pressure of at least about 1 torr to effect the recovery of organic carbonate free of color bodies, and (4) recovering palladium cocatalyst system values from the residue of (3).

The palladium material or catalyst useful in the practice of the present invention can be in elemental form, or it can be employed as a palladium compound. Accordingly, palladium black, metallic or amorphous palladium, or palladium compounds deposited on an inert support such as carbon can be used as well as palladium compounds, for example, halides, nitrates, carboxylates, and complexes of palladium involving such compounds as carbon monoxide, amines, phosphines or olefins. The preferred palladium compounds are palladium (II) salts of organic acids including carboxylates with $C_{2-6}$ aliphatic acids. Palladium (II) acetate is particularly preferred. The tetraalkylammonium halides which can be used are the chlorides and bromides and preferably the bromides. The alkyl groups of the alkylammonium halides can be primary and secondary alkyl and have from 1-8 carbon atoms. Tetra-n-butylammonium bromide, tetramethylammonium bromide and tetraethylammonium bromide are particularly preferred.

The metallic cocatalyst materials which can be used include cobalt and manganese compounds. These compounds can be divalent or trivalent, and include salts, such as halides and carboxylates and complexes with amines, phosphines, diketones and carbon monoxide. Cobalt (II) acetate is particularly preferred. In addition to cobalt and manganese, iron salts, such as ferrocene and ferric chloride, copper salts such as copper acetate, copper bromide, copper acetoacetonate, and cerium salts such as, cerium (III) chloride, cerium bromide and cerium acetate can be used.

The organic cocatalysts include aromatic ketones such as benzophenone, acetophenone and 2-methoxyacetophenone and aliphatic ketones, such as methyl isobutyl ketone (MIBK) and aromatic polycyclic coal tar hydrocarbons, for example, anthracene, pyrene, chrysene, phenanthrene, 1.10-phenanthroline and naphthacene.

The organic hydroxy compound used in the practice of the present invention can be selected from aliphatic, alicyclic and aromatic mono or polyhydroxy compounds, such as methanol, ethanol, butanol, cyclohexanol, phenol, cresol, xylenol, ethylene glycol, propylene glycol, resorcinol, hydroquinone, and bisphenol A. Aromatic hydroxy compounds are preferred and phenol is particularly preferred.

Palladium can be used in an amount equivalent to about 1 g-atom of Pd, per 200-20,000 moles of organic hydroxy compound. The metallic cocatalyst, for example, cobalt or manganese can be used at about 0.1-5 g-atoms of metallic cocatalyst, per g-atom of palladium. The tetraalkylammonium halide can be used in the carbonylation mixture in an amount sufficient to provide about 0.01-100 moles of tetraalkylammonium halide, per g-atom of palladium. The organic cocatalyst, such as benzophenone, can be used in an amount sufficient to provide from 0.01-50 moles of organic cocatalyst, per g-atom of palladium.

In addition to the aforementioned ingredients, there can be utilized desiccants such as carbon dioxide which can be employed in an amount sufficient to provide from about 0.01 to about 50 moles of carbon dioxide, per mole of organo hydroxy compound. In addition to carbon dioxide, molecular sieves also can be used as a drying agent.

In the practice of the preferred form of the invention, the reactants, such as the organo hydroxy compound, carbon monoxide, and oxygen containing gas, for example, air or oxygen, and the catalyst components, for example, the palladium catalyst material, the quaternary ammonium salt, metallic cocatalyst and organic cocatalyst along with or without a suitable desiccant, can be initially introduced into the reactor. Contact between the various components can be effected under high pressure and temperature as previously defined. The partial pressures of carbon monoxide and oxygen can at least be about 50 psi to 3000 psi with a preferred partial pressure being in the range of about 500 to 2000 and about 50 psi to 300 psi, respectively.

In instances where carbon dioxide is employed as a desiccant there can be utilized under ambient conditions from about 0.01 to 50 moles of carbon dioxide, per mole of organic hydroxy compound.

In certain instances, solvents can be employed in the reaction including aliphatic, alicyclic and aromatic hydrocarbons, such as hexane, heptane, cyclohexane, decane, toluene and xylene; acetonitrile; halogenated hydrocarbons, such as methylene chloride, chloroform and chlorobenzenes; ethers, such as diphenyl ether, diglyme and dioxane; dimethyl formamide; and esters, such as ethyl acetate or methyl formate. In addition to carbon dioxide, other drying agents such as activated alumina, calcium sulfate, calcium chloride, anhydrous carbon or charcoal, and molecular sieves can be used.

At the termination of the reaction, residual organic hydroxy compound, such as phenol, can be readily removed by distillation at pressures of 1 torr to atmospheric. In instances where phenol is used, it is preferred to use pressures of 1 torr to 15 torr at temperatures of 55° C. to 125°C.

Recovery of the organic carbonate free of color bodies can be achieved at pressures from about 1 torr to atmospheric and preferably 15 torr to 45 torr in instances where diphenyl carbonate is distilled. Temperatures in the range of 120° C. to 325° C. can be used, and preferably 155° C. to 302° C.

Recycling of the palladium catalyst and cocatalyst components can be thereafter effected from the distillation residue.

In order that those skilled in the art will be better able to practice the present invention, the following examples are given by way of illustration and not by way of limitation. All parts are by weight.

EXAMPLE 1

There is added into a reactor, 50.0 g (0.531 mol), of phenol, 1.50 g (4.65 mmol) of tetrabutylammonium bromide (TBAB), 0.050 g (0.222 mmol) of palladium diacetate (Pd(OAc)$_2$), 0.035 g (0.198 mmol) of cobalt diacetate (Co(OAc)$_2$) and 0.750 g (4.12 mmol) of benzophenone. The reactor is sealed and charged with 900 psi CO$_2$, for leak testing, and then is exhausted to atmospheric pressure. The reactor is then flushed with 2×1500 psi CO followed by pressurization to psi with CO (high pressure leak test) and is exhausted back to atmospheric pressure. The reactor is further flushed with 4×1500 psi O$_2$. At the end of the fourth oxygen purge cycle, the oxygen atmosphere in the reactor is reduced to 300 psig. There is then added to the oxygen atmosphere, 400 psi of CO$_2$ and 900 psi of CO. The reactor is then heated to 100° C. Aliquots are taken at predetermined times to assess the amount of diphenyl carbonate which is produced. After each sampling, the reactor atmosphere is rejuvenated by exhausting the atmosphere to 1000 psi (P$_f$), followed by the addition of 200 psi of O$_2$ and 700 psi of CO. After 5 hours there is obtained a brown mixture containing 11.36% of diphenyl carbonate based on GC.

The reaction solution is distilled at 100° C. at 15 torr to effect the removal of phenol. The residue is then distilled at 160–165° C. at 15 torr to effect the recovery of diphenyl carbonate. There is obtained 6–9% yield of substantially white diphenyl carbonate.

After the reaction mixture is vacuum distilled over a period of about 3 hours at 1 torr reaching a temperature of 150° C., there is obtained a dark solid metal residue. It is placed in a ceramic container and heated at 700° C. in air for 16 hours. Elemental analysis of the residue shows that the residue consists of about 32% by weight palladium and about 13% by weight of cobalt. The residue is mechanically ground to a fine powder to produce active carbonylation catalyst.

EXAMPLE 2

In accordance with the procedure of Example 1, there is added into a reactor 50.0 g (0.531 mol) of phenol, 1.30 g (4.04 mmol) of TBAB, 0.035 g (0.156 mmol) of Pd (OAc)$_2$, 0.035 mg; (0.188 mmol) of ferrocene and 0.275 g; (2.54 mmol) of benzophenone. The reactor is sealed, it is charged with 900 psi $CO_2$, leak-checked and then it is exhausted to atmospheric pressure. The reactor is flushed 2×1500 psi CO followed by pressurization to 2100 psi with CO for exhausting it back to atmospheric pressure. The reactor is flushed 4×1500 psi $O_2$; at the end of the fourth oxygen purge cycle, the oxygen atmosphere in the reactor is reduced to 300 psig. There is added 400 psi of $CO_2$ and 900 psi of CO. The reactor is heated to 100° C. Periodic aliquots are removed after each sampling, the reactor is rejuvenated by exhausting the atmosphere to 1000 psi (Pt), followed by the addition of $O_2$ (200 psi) and CO (700 psi). After 2 hours of sampling there is obtained 4.34% of colored diphenyl carbonate based on phenol. The reaction solution is distilled at 100° C. at 15 torr to effect the removal of phenol. The residue is then distilled at 160-165° C. at 15 torr to effect the recovery of diphenyl carbonate. There is obtained 2-4% yield of substantially pure diphenyl carbonate. The procedure of example (1) is used to provide the recovery of active palladium catalyst values.

EXAMPLE 3

In accordance with the procedure of Example 1, there is added to a reactor, 50.0 g (0.531 mol) of phenol, 1.5 g (4.65 mmol) of TBAB, 0.060 g (0.267 mmol) of Pd(OAc)$_2$, 0.045 g (0.254) of Co (OAc)$_2$ and 0.400 g (2.24 mmol) of anthracene. The reactor is sealed and charged with 900 psi $CO_2$, leak-checked and then exhausted to atmospheric pressure. The reactor is flushed 2×1500 psi of CO followed by pressurization to 2100 psi with CO (high pressure leak test) before exhausting it back to atmospheric pressure. The reactor is flushed with 4×1500 psi $O_2$; at the end of the fourth oxygen purge cycle, the oxygen atmosphere in the reactor is reduced to 300 psig. There is added to the oxygen atmosphere, 400 psi of $CO_2$ and 900 psi of CO. The reactor is heated to 100° C. Aliquots are taken at predetermined times to assess the amount of diphenyl carbonate which has been produced. After each sampling, the reactor atmosphere is rejuvenated by exhausting the atmosphere to 1000 psi (P$_t$) followed by the addition of $O_2$(200 psi) and CO (700 psi). After 6 hours of reaction, there is obtained 10.75% yield of a red-brown diphenyl carbonate. The reaction solution is then distilled at 90–105° C. at 15 torr to effect the removal of phenol. The residue is then distilled at 160–165° C. at 15 torr to effect the recovery of diphenyl carbonate. There is obtained 7–10% yield of substantially white diphenyl carbonate. The procedure of example (1) is used to provide the recovery of active catalyst values.

There is charged 900 psi of $CO_2$ into a reactor which is leak checked and then exhausted to atmospheric pressure. The reactor contains a mixture consisting of 50.0 g (0.531 mol) of phenol, 1.50 g (4.65 mmol) of TBAB, 0.55 g (0.245 mmol) of Pd(OAc)$_2$, 0.040 g (0.226 mmol) of Co(OAc)$_2$ and 0.340 g (2.02 mmol) of 2'-methoxyacetophenone. The reactor is then flushed with 2×1500 psi CO followed by pressurization to 2100 psi with CO (high pressure leak test) before exhausting it back to atmospheric pressure. The reactor is flushed with 4×1500 psi $O_2$; at the end of the fourth oxygen purge cycle, the oxygen atmosphere in the reactor is reduced to 300 psig. There is added to the oxygen atmosphere, 400 psi of $CO_2$ and 900 psi of CO. The reactor is heated to 100° C. Aliquots are taken at predetermined time to assess the amount of diphenylcarbonate which has been produced. After each sampling, the reactor atmosphere is rejuvenated by exhausting the atmosphere to 1000 psi (P$_t$), followed by the addition of 200 psi of $O_2$ and 700 psi of CO. After 6 hours there is obtained 10.75% by weight of a red-brown diphenyl carbonate product.

The reaction solution is distilled at 90–105° C. at 15 torr to effect the removal of phenol. The residue is then distilled at 160–165° C. at 15 torr to effect the recovery of diphenyl carbonate. There is obtained 7–10% yield of substantially white diphenyl carbonate. The procedure of example (1) is used to provide the recovery of active catalyst values.

EXAMPLE 5

There is placed in an autoclave, 50.0 g (0.531 mmol) of phenol, 1.50 g (4.65 mmol) of TBAB, 0.045 g (0.200 mmol) of Pd(OAc)$_2$, 0.050 g (0.203 mmol) of anhydrous cerium dichloride and 0.300 g (2.78 mmol) of benzophenone. The reactor is sealed, charged with 900 psi of $CO_2$, leak checked and then exhausted to atmospheric pressure. The reactor is then flushed with 2×1500 psi of CO followed by pressurization to 2100 psi with CO (high pressure leak test) before exhausting it back to atmospheric pressure. The reactor is flushed 4×1500 psi $O_2$ and at the end of the fourth oxygen purge cycle, the oxygen atmosphere in the reactor is reduced to 300 psig. There is added to the oxygen atmosphere, 400 psi of $CO_2$ and 900 psi of CO. The reactor is heated to 100° C. Aliquots are taken from the reactor periodically to monitor diphenylcarbonate production. After each sampling the reactor atmosphere is rejuvenated by exhausting the atmosphere to 1000 psi (P$_t$) followed by the addition of 200 psi of oxygen and 700 psi of CO. There was obtained after 5 hours, a 3.26% yield of brown diphenylcarbonate.

The reaction solution is distilled at 90–105° C. at 15 torr to effect the removal of phenol. The residue is then distilled at 160–165° C. at 15 torr to effect the recovery of diphenyl carbonate. There is obtained 1–3% yield of substantially white diphenyl carbonate. Following the procedure of example 1, active metallic catalyst values are recovered from the distillate residue.

EXAMPLE 6

There is introduced into an autoclave, 35.0 g (0.372 mol) of phenol, 1.14 g (3.54 mmol) of TBAB, 0.028 g (0.125 mmol) of Pd(OA)$_2$, 0.018 g (0.102 mmol) of Co-(OAc)$_2$, 2.00 g (19.97 mmol) methyl isobutyl ketone (MIBK) and 35 g (261 mmol) of 2-methoxyethyl ether (diglyme). The reactor is sealed, charged with 900 psi $CO_2$, leak-checked, and then exhausted to atmospheric pressure. The reactor is flushed 2×1500 psi CO followed by pressurization to 2100 psi with CO (high pressure leak test) before exhausting the reactor back to atmosphere pressure. The reactor is flushed with 4×1500 psi of $O_2$ and at the end of the fourth oxygen purge cycle, the oxygen atmosphere in the reactor is reduced to 300 psig. There is added to the oxygen atmosphere, 400 psi of $CO_2$ and 900 psi of CO. The reactor is heated to 100° C. Aliquots of the mixture are taken at predetermined times to determine the amount of diphenyl carbonate which has been produced. After each sampling, the reactor atmosphere is rejuvenated by exhausting the atmosphere to 1000 psi ($P_t$) followed by the addition of 200 psi of oxygen and 700 psi of carbon monoxide. After 5 hours of reaction there is obtained an 11.41% yield of a red-brown diphenyl carbonate. The reaction solution is distilled at 95–110° C. at 15 torr to effect the removal of phenol. The residue is then distilled at 155–165° C. at 15 torr to effect the recovery of diphenyl carbonate. There is obtained 6–10% yield of substantially white diphenyl carbonate. Following the procedure of example 1, active metallic catalyst values are recovered from the distillate residue.

EXAMPLE 7

To a 300ml Parr® stirred pressure reactor (autoclave) at room temperature are added phenol (50.2 g; 0.533 mol), diphenyl ether (DPE; 6.710 g; 39.4 mmol), tetrabutylammonium bromide (TBAB; 1.720 g; 5.34 mmol), benzophenone (0.325 g; 3.01 mmol), 38 mg of palladium catalyst recovered from example 1, and Co(OAc)$_2$ (27 mg; 0-153 mmol). The reactor vessel is sealed, and the internal atmosphere above the mixture is purge-exchanged 4×400 psi with gaseous carbon dioxide ($CO_2$) and is then charged with $O_2$ (400 psi), $CO_2$ (400Psi), and CO (800 psi) yielding a total pressure of 1600 psi. After pressurization, the reactor is heated to 100° C. The reaction solution is stirred at approximately 540–550 rpm to ensure efficient aeration of the reaction mixture. Aliquots are taken periodically from GC analysis in order to quantify the amount of diphenyl carbonate produced. The reaction atmosphere is rejuvenated periodically by exhausting the vessel down to 1000 psi followed by recharging with $O_2$ (300 psi) and CO (600 psi); the rejuvenation cycles and GC analyses are performed at the following times: 0.5, 1.0, 2.0, 3.0 (no rejuvenation), and 4.0 h. The reaction solution exhibits less than 0.75% diphenyl carbonate formation during the first 2 hours. The diphenyl carbonate yield climbs to 0.866 g (1.5%) by the three hour point. At 4 h, the yield of diphenyl carbonate is 1.79 g (3.1%). By the end of the reaction (5 h), the yield of diphenyl carbonate has reached 3.58 g (6.2%). The diphenyl carbonate is recovered following the procedure of example (1).

Although the above examples are directed to only a few of the very many variables which can be used in the practice of method of the present invention, it should be understood that the present invention is directed to the employment of a much broader variety of inorganic cocatalyst, such as ferracene and organic cocatalyst, such as anthracene as set forth in the description preceding these examples.

What is claimed is:

1. A method for making an aromatic carbonate which comprises,
   (1) contacting an aromatic hydroxy compound with a mixture of carbon monoxide and oxygen at a temperature of from about 50° C. to about 170° C. and at a pressure from about 100 psi to about 5000 psi in the presence of a palladium containing catalyst comprising,
      (a) palladium material
      (b) a quaternary ammonium salt,
      (c) a metallic cocatalyst material selected from a class of metals or compounds of metals consisting of cobalt, iron, cerium, manganese, molylidenum, samarium, vanadium, chromium and copper, and,
      (d) an organic catalyst selected from a member of the class consisting of aromatic ketones, aliphatic ketones and aromatic polycyclic coal tar hydrocarbons,
   (2) distilling the mixture of (1) at a temperature of at least about 45° C. and at a pressure of at least about 1 torr to effect removal of the aromatic hydroxy compound,
   (3) distilling the mixture of (2) at a temperature of at least about 120° C. and at a pressure of at least about 1 torr to effect the recovery of aromatic carbonate free of color bodies, and
   (4) recovering palladium containing catalyst values from the residue of (3).

2. A method for making an aromatic carbonate in accordance with claim 1, where the aromatic hydroxy compound is phenol.

3. A method in accordance with claim 1, where the palladium material is palladium (II) acetate.

4. A method in accordance with claim 1, where the quaternary ammonium salt is tetrabutylammonium bromide.

5. A method in accordance with claim 1, where the metallic cocatalyst is cobalt acetate.

6. A method in accordance with claim 1, where the organic cocatalyst is benzophenone, anthracene, 1,10-phenanthroline, or 2'-methoxyacetophenone.

7. A method in accordance with claim 1, where the metallic cocatalyst is ferrocene.

* * * * *